United States Patent
Shoher et al.

(10) Patent No.: US 9,295,533 B2
(45) Date of Patent: Mar. 29, 2016

(54) MATERIAL FORMING A DENTAL COPING IN THE PREPARTION OF A DENTAL RESTORATION

(76) Inventors: Itzhak Shoher, Herzelia (IL); Aharon Whiteman, Petach Tikvah (IL)

(*) Notice: Subject to any disclaimer, the term of this patent is extended or adjusted under 35 U.S.C. 154(b) by 1422 days.

(21) Appl. No.: 11/586,081

(22) Filed: Oct. 26, 2006

(65) Prior Publication Data

US 2008/0098852 A1    May 1, 2008

(51) Int. Cl.
| | |
|---|---|
| B22F 1/00 | (2006.01) |
| B22F 3/11 | (2006.01) |
| B22F 3/26 | (2006.01) |
| A61C 13/00 | (2006.01) |
| A61K 6/00 | (2006.01) |
| A61K 6/04 | (2006.01) |
| C22C 1/04 | (2006.01) |

(52) U.S. Cl.
CPC ........... *A61C 13/0003* (2013.01); *A61K 6/0023* (2013.01); *A61K 6/046* (2013.01); *B22F 1/0003* (2013.01); *B22F 3/1121* (2013.01); *B22F 3/26* (2013.01); *C22C 1/0466* (2013.01); *B22F 2999/00* (2013.01)

(58) Field of Classification Search
CPC ................ B22F 2301/25; B22F 2301/255
USPC ........... 75/300, 228, 229, 230, 255, 392, 414, 75/415, 585, 631–637, 746, 747, 751, 765, 75/767, 769, 770, 772, 955; 148/513, 400, 148/430; 419/1, 2, 10, 26, 27, 30, 36, 47, 419/61, 62, 65, 66; 420/463, 465, 466, 580
See application file for complete search history.

(56) References Cited

U.S. PATENT DOCUMENTS

| | | | |
|---|---|---|---|
| 4,742,861 A | 5/1988 | Shoher et al. | |
| 4,814,008 A | 3/1989 | Shoher et al. | |
| 4,990,394 A | 2/1991 | Shoher et al. | |
| 5,234,343 A | 8/1993 | Shoher et al. | |
| 5,272,184 A * | 12/1993 | Shoher et al. | 523/118 |
| 5,336,091 A | 8/1994 | Shoher et al. | |
| 5,593,305 A * | 1/1997 | Shoher et al. | 433/218 |
| 5,914,185 A * | 6/1999 | Shoher et al. | 428/323 |

OTHER PUBLICATIONS

W.H. Qi, et al., Size and shape dependent melting temperature of metallic nanoparticles, Materials Chemistry & Physics 88 (2004) 280-284.
Melting-point depression, Wikipedia, the free encyclopedia, May 10, 2011, pp. 1-8.

* cited by examiner

*Primary Examiner* — Scott Kastler
*Assistant Examiner* — Vanessa Luk

(57) ABSTRACT

A material composition for use in forming a porous metal structure and dental coping in the preparation of a dental restoration comprising a composite of metal particles in a matrix including low fusing temperature metal particles and at least between 35 to 85% medium fusing temperature metal particles by volume with the medium fusing temperature metal particles possessing a melting characteristic which during heat treatment of the material composition to form the porous metal structure results in partial melting of the medium fusing temperature metal particles to the extent of between about 4% to 50% by volume of the particle mass of each medium fusing temperature metal particle.

7 Claims, No Drawings

US 9,295,533 B2

MATERIAL FORMING A DENTAL COPING IN THE PREPARTION OF A DENTAL RESTORATION

FIELD OF THE INVENTION

This invention relates to a dental material composition for use in forming a porous metal structure and dental coping in the preparation or repair of a dental restoration.

BACKGROUND OF THE INVENTION

In crown and bridge prosthodontics, metal copings are conventionally used to form the understructure of a dental restoration such as a crown and/or bridge. The metal coping must provide the required structural strength and rigidity necessary for the restoration to resist the forces of mastication when chewing food. In a ceramic-to-metal dental restoration the metal coping is covered with a fired-on coating of porcelain or acrylic for purposes primarily of aesthetics. Desirably, the metal coping should also provide a biocompatible relationship with the gingival tissue at the margin of the dental restoration.

Traditionally the dental coping was formed from cast metal using a conventional casting operation. Over the past twenty years a substitute procedure using a base composition of metal particles to form the dental coping has been introduced to the dental profession and has become widely accepted as a replacement for the traditional cast coping. In this substitute procedure the base composition of metal particles is shaped and/or molded over a die into a desired configuration and then heat treated into a porous structure which forms the dental coping upon the incorporation of a filler material pursuant to a subsequent heat treatment operation. The addition of filler material is required to solidify the porous structure into a solid mass representative of the finished dental coping before placement of the dental coping in the mouth of the patient. The dental material of choice for forming a dental coping in this manner is "Captek", a registered trademark of Precious Chemicals Inc., which is a composition comprising noble metal particles as taught and described in U.S. Pat. Nos. 4,742,861; 4,814,008; 4,990,394; 5,234,343 and 5,336,091 the disclosures of which are herein incorporated by reference.

As described in the aforementioned patents a dental coping is formed from a base material composition comprising a combination of high fusing temperature metal particles and low fusing temperature metal particles combined in a matrix which should preferably include a volatile binder. Other minor constituents may be included such as particles of activated carbon. The high and low fusing temperature metal particles are selected to provide a melting characteristic which lies respectively above and below the heat treatment temperature to which the metal composite is to be subjected for forming the dental coping. Accordingly, the low fusing temperature metal particles should have a melting temperature to cause the particles of low fusing metal to melt at or below the selected heat treatment temperature whereas the high fusing temperature metal particles should have a melting temperature above the selected heat treatment temperature so that they essentially will not melt during heat treatment. The volatile binder may be composed of a material such as dental wax which should vaporize during heat treatment. The heat treatment process may involve more than one heat treatment step using different heat treatment temperatures or may involve use of a graduated temperature. In this instance the high and low fusing temperature metal particles are still distinguished from one another by the fact that the low fusing temperature metal particles should all melt during heat treatment whereas the high fusing temperature metal particles essentially do not melt during heat treatment. Since heat treatment occurs over a given time interval which is variable little or no melting of the high fusing metal particles should occur despite the selected time interval of heat treatment or the porous structure formed during heat treatment will shrink and result in failure.

Although this relatively new dental material and procedure for forming a dental coping has received wide acceptance in the dental profession a considerable amount of expertise is presently required of the dental laboratory technician or dentist in using the material to properly shape the material on the die particularly at the margin and to heat treat the material. The necessity to acquire such expertise has inhibited many laboratories and single practitioners from using this material and procedure on a consistent basis. Obviously, a dental material which would require less expertise for forming the dental coping would increase the desirability for using such material in the preparation of a dental restoration and/or to repair existing restorations.

The dental composition of the present invention is a modification in the formulation of the matrix of metal particles taught in the aforementioned patents and represents a substantial improvement in that the material composition of the present invention allows the material to be shaped and heat treated with much less expertise and little or no follow up supervision.

SUMMARY OF THE INVENTION

The dental material of the present invention is a composition comprising a composite of metal particles in a matrix of metal particles including low fusing temperature metal particles and at least between 35% to 85%, preferably 65%, medium fusing temperature metal particles by volume with the medium fusing temperature metal particles possessing a melting characteristic during heat treatment for causing the medium fusing temperature metal particles to partially melt over a heat treatment time of between 1 to 10 minutes, preferably 3 to 6 minutes, at between 1000° C. and 1200° C. such that all of the low fusing temperature metal particles have melted and by the end of heat treatment at least substantially all of the medium fusing temperature metal particles have partially melted to a limited extent wherein about 4% to 50% by volume of the particle mass of each such medium fusing temperature metal particle has melted with the low fusing temperature metal particles representing the remainder of the composition of metal particles or including a relatively minor percentage of high fusing temperature metal particles. The medium fusing particles and high fusing temperature metal particles, if included, should be thin and of non-spherical geometry and preferably in the form of thin flakes having one or more jagged edges.

By limiting the extent to which all or substantially all of the medium fusing particles melt during heat treatment so that no more than 50% by volume of each such particle melts and preferably between 10 to 25% by volume of each such particle melts a porous skeleton structure will form which will not shrink as a result of heat treatment and will require little or no training to use. However it is essential to the present invention that all or substantially all of the medium fusing particles at least partially melt during heat treatment to the extent that above about 4% by volume of each such particle has melted but less than 50% of its volume and preferably between 10 to 25% with 10 to 15% being optimum. The controlled partial melting of the medium fusing particles permits the material to be shaped or molded to the die even at the margins without shrinkage. The melted portion of each of the medium fusing particles combine and fuse with the melted low fusing particles to enhance the properties particularly the temperature stability of the porous structure formed from the non-melted portion of the medium fusing particles. The composition can comprise medium temperature fusing particles alone or in combination with high fusing particles. Moreover, more than one composition of medium fusing particles may be used to provide greater control over the partial melting characteristic of the total medium fusing particle content in the dental material composition.

DETAILED DESCRIPTION OF THE INVENTION

The present invention is a moldable dental material which, in general, is taught in U.S. Pat. Nos. 4,742,861; 4,814,008; 4,990,394; 5,234,343 and 5,336,091 the disclosures of which are herein incorporated by reference for forming, repairing or restoring dental restorations using any conventional stone, metal or polymer non-refractory or refractory working die.

More specifically the dental material of the present invention is a moldable composition comprising medium fusing temperature metal particles alone or in combination with high fusing temperature metal particles, low-fusing temperature metal particles and a volatile binder. Upon heat treatment, the binder should vaporize forming a porous, three dimensional skeleton or sponge-like structure having a capillary network of multiple voids uniformly distributed throughout the structure, with a void volume preferably above about twenty percent (20%), and up to a void volume of eighty percent (80%).

The binder may be any suitable vehicle which will vaporize upon heat treatment, to facilitate the formation of a porous structure. The preferred binder is composed substantially or entirely of wax, with the remainder, if any, of an organic or hydrocarbon compound to control the malleability of the dental material. The term "wax," for purposes of the present invention, means any natural wax, mineral wax, or organic wax, or combination thereof. The concentration of the binder is preferably high enough to assure a void volume of at least twenty percent (20%). In addition to the metal particles and binder, the dental material should preferably contain a small amount of carbonaceous particles of preferably activated carbon in an amount of between five-thousands of one percent (0.005%) of the weight of the metal mixture, to about two percent (2%) of the weight of the metal mixture, with 0.05 wt. % to 0.5 wt. % being preferred.

The component of medium fusing temperature metal particles is critical to the composition of metal particles in the dental material of the present invention. The medium fusing temperature metal particles are selected primarily or entirely from noble metals and will possess a melting characteristic during heat treatment within a heat treatment temperature range of between 1000° C. and 1200° C. for causing all or substantially all of the medium fusing temperature metal particles to partially melt over a heat treatment time of between 1 to 10 minutes, preferably 3 to 6 minutes, such that at the end of heat treatment the medium fusing temperature metal particles have partially melted but only to a limited extent. To satisfy this requirement it is essential to melt between about 4% to 50% by volume of the particle mass of each medium fusing temperature metal particle during heat treatment. The extent of melting of the medium fusing particles can be determined and verified with relative accuracy using a scan electron microscope having at least a 3 to 5 nanometer resolution and preferably a resolution of between 1 to 2 nanometers. A porous skeleton structure of high density will be formed by the residual non-melted portion of the medium fusing particles. If the medium fusing particles melt in excess of 50% by volume the skeleton structure will shrink during heat treatment. In general, a structure which shrinks during heat treatment is considered detrimental and preferably no shrinkage at all should take place during heat treatment. This is achieved in accordance with the present invention by limiting the amount of melting of the medium fusing particles to between 10 and 25% by volume of each medium fusing particle. Conversely, some partial melting of each of the medium fusing particles during heat treatment has been found essential for causing the melted portion of the medium fusing particles to combine with the melting low fusing particles and form a melt mixture which stabilizes the formation of the porous structure even at the margins. Partial melting requires melting of the medium fusing particles to the extent of at least about 4% by volume, preferably between 10 and 25% by volume and optimally between 10 to 15%. By stabilizing the formation of the porous structure the dental material does not require any degree of skill to apply and mold to the die prior to heat treatment.

To the extent that some of the medium fusing particles do not melt these, in essence, are equivalent to high fusing temperature metal particles. Alternatively, high fusing temperature metal particles may be included in the mixture of metal particles but should be limited to no more than about twenty (20)% by volume of the mixture in the material composition and preferably less than 10% by volume.

At least 35% to 85% by volume of the mixture of metal particles in the material composition should consist of medium fusing temperature metal particles with the remainder consisting of low fusing temperature metal particles or a combination of low fusing temperature metal particles and a limited amount of high fusing temperature metal particles. In general between 30 to 60% of the mixture of particles will consist of low fusing temperature metal particles but preferably no more than about 50% low fusing temperature metal particles.

As indicated above the composition of the medium fusing temperature metal particles should be selected from noble metals and preferably platinum and palladium in any desired proportion to one another from zero to one hundred percent in addition, gold may be primarily added although other metal constituents to a smaller degree may also be added such as Ag, Cu, Mg, Al, Zn and Re. Moreover, other metals of the platinum group of elements of the third and fourth group of elements may be added. It is the proportion of gold and the other constituents which will control the melting characteristic of the medium fusing temperature metal particles such that each of the medium fusing particles will partially melt to within a controlled degree as explained heretofore. Alternatively, more than one medium fusing particle composition may be used to provide greater control over the partial melting characteristic of the total medium fusing particle content in the dental material composition of the present invention. For example, two or more medium fusing particle compositions may be used to form the total medium fusing component of the mixture of metal particles with one of the compositions constituting a major or primary portion of between 75 to 95% of the total medium fusing component and the others representing a minor or secondary portion. The major portion may contain more gold than the other secondary portions and/or the secondary portions may contain harder materials such as titanium, rhodium, strontium and possibly stainless steel can be judiciously added to provide a different melting percentage for the secondary portions relative to the primary portion over the given time period within the heat treatment period.

The medium fusing particles should have an irregular shape preferably in the form of flakes such as platelets and should be thin and flat. However, it is preferred that the thin flakes also have jagged edges. The existence of jagged edges provides greater interlocking or interleaving of particles during heat treatment.

The low fusing particles are composed preferably of gold or a gold alloy, with gold as the major constituent. The preference for gold as the major constituent of the low-fusing component is based on its known characteristics of workability, biocompatibility, non-oxidizing properties, and color. The low-fusing metal particles must melt during heat treatment for forming the porous structure.

It should be understood that heat treatment may occur in stages at different temperatures over a temperature range of between 1000° C. and 1200° C. However, the medium fusing particles should possess a melting characteristic during heat treatment over a heat treatment time of between 1 to 10 minutes, preferably 3 to 6 minutes, such that at the end of such heat treatment substantially all of the medium fusing temperature metal particles have partially melted as explained above.

Following the formation of the porous structure a filler material is melted into the voids of the porous structure to solidify the structure and form the finished dental coping. The filler material may be any suitable ceramic or metal composition, preferably a precious metal composition. The filler material may also be formed of a matrix of particles mixed with a wax binder or mixed with a liquid vehicle to help spread it. The filler material binder may have a composition and concentration similar to the composition and concentration of the binder used in the dental material to form the porous structure.

What is claimed:

1. A material composition for use in forming a porous metal structure of high void volume during heat treatment between about 1000° C. to about 1200° C. in the preparation of a dental restoration comprising a volatile binder and a composite of metal particles in a matrix including low fusing temperature metal particles which melt at said heat treatment temperature, zero to a relatively minor percentage of high fusing temperature metal particles, which will not melt at said heat treatment temperature and between 65% to 85% medium fusing temperature metal particles by volume with the medium fusing temperature metal particles having a non-spherical platelet shape of thin cross-section, and a jagged edge curvature possessing a melting characteristic which will cause partial melting of all of the medium fusing temperature metal particles during heat treatment of the material composition at said heat treatment temperature and over a heat treatment time of between 1 to 10 minutes such that between 10% to 50% by volume of the particle mass of each the medium fusing temperature metal particles melt during heat treatment and wherein the volatile binder burns off and all of the low fusing temperature metal particles completely melts during heat treatment leaving a residual metal composition of the non-melted portion of the medium fusing temperature metal particles alone or in combination with the relatively minor percentage of high fusing temperature metal particles, if present, for forming a porous skeleton structure of high density.

2. A material composition as defined in claim 1 wherein said medium fusing temperature metal particles comprises noble metals selected from the group consisting of platinum and palladium in any desired proportion and a minor percentage of one or more of the following metals: Ag, Cu, Mg, Al, Zn and Re.

3. A material composition as defined in claim 2 wherein the dental material includes at least two medium fusing temperature metal particle compositions with one composition constituting a major or primary portion of between 75% to 95% of the total medium fusing component and the other a minor or secondary portion.

4. A material composition as defined in claim 1 wherein said medium low fusing temperature metal particles partially melt during heat treatment at a heat treatment time of between 3 to 6 minutes.

5. A material composition as defined in claim 4 wherein a filler material is melted into the voids of the porous structure following heat treatment composed of any suitable ceramic or metal composition to form a solidified dental coping.

6. A material composition as defined in claim 5 wherein the dental material includes at least two medium fusing temperature metal particle compositions with one composition constituting a major or primary portion of between 75 to 95% of the total medium fusing component and the other a minor or secondary portion.

7. A material composition as defined in claim 6 wherein said secondary portion includes additional harder materials selected from the group consisting of titanium, rhodium, strontium and stainless steel to control the melting percentage of the secondary portion relative to the primary portion.

* * * * *